United States Patent
Pelc et al.

(10) Patent No.: US 7,103,138 B2
(45) Date of Patent: Sep. 5, 2006

(54) SAMPLING IN VOLUMETRIC COMPUTED TOMOGRAPHY

(75) Inventors: Norbert J. Pelc, Los Altos, CA (US); Taly Gilat Schmidt, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 10/925,867

(22) Filed: Aug. 24, 2004

(65) Prior Publication Data

US 2006/0045234 A1    Mar. 2, 2006

(51) Int. Cl.
*A61B 6/03* (2006.01)

(52) U.S. Cl. .............................................. 378/9; 378/4
(58) Field of Classification Search ................... 378/4, 378/12–15, 122, 208, 209, 9
See application file for complete search history.

(56) References Cited

U.S. PATENT DOCUMENTS

| | | | | |
|---|---|---|---|---|
| 5,467,377 A | | 11/1995 | Dawson | 378/19 |
| 5,625,661 A | * | 4/1997 | Oikawa | 378/15 |
| 5,841,831 A | * | 11/1998 | Hell et al. | 378/19 |
| 5,966,422 A | | 10/1999 | Dafni et al. | 378/9 |
| 6,212,251 B1 | * | 4/2001 | Tomura et al. | 378/15 |
| 6,229,870 B1 | * | 5/2001 | Morgan | 378/9 |
| 6,580,777 B1 | | 6/2003 | Ueki et al. | 378/17 |
| 2005/0100126 A1 | * | 5/2005 | Mistretta et al. | 378/15 |

* cited by examiner

*Primary Examiner*—Edward J. Glick
*Assistant Examiner*—Hoon Song
(74) *Attorney, Agent, or Firm*—Lumen Intellectual Property Services Inc.

(57) ABSTRACT

A volumetric computed tomography method includes translating a discrete element x-ray source and detector relative to the patient or object in a z-direction parallel to the axis of rotation. As the source rotates through the angles of a single rotation, it is simultaneously translated by a distance comparable to the discrete spacing distance between individual source elements in the z-direction. The small translation is designed so that the axial planes passing through discrete source element rows are not distinguished from axial planes passing between the discrete source element rows, thereby eliminating the z-dependence of the system and associated sampling problems.

13 Claims, 2 Drawing Sheets

SAMPLING IN VOLUMETRIC COMPUTED TOMOGRAPHY

FIELD OF THE INVENTION

The invention relates to scanning methods for use in volumetric computed tomography systems that have a plurality of discrete source elements displaced in the z-direction (i.e., the axial direction). This may include, for example, systems with a linear array of source elements forming a single column of individual sources displaced from each other in the z-direction, or a 2-D array of source elements forming multiple discrete rows of sources displaced from each other in the z-direction.

BACKGROUND OF THE INVENTION

In the prior art, volumetric computed tomography (VCT) systems are conventionally operated by rotating the source and detector around a rotational axis (often called the z-axis), thereby obtaining image measurements from multiple angles. These measurements are then computationally combined to create a three-dimensional representation of an object within the field of view of the system. Many such systems have a single x-ray source that travels in a circular path as the system rotates. It is known that such systems suffer from "cone-beam" artifacts. To avoid these artifacts, some VCT systems use a source with an array of source elements separated in the axial direction. The length of the source and detector in the axial direction defines an axial extent of a VCT system. If the source and detector movement is limited to rotation, then the axial extent corresponds to the axial field of view, i.e., the total thickness of the volume acquired by the system during an entire rotation. However, the axial field of view of a CT system can be made larger than the axial extent by introducing a translation of the source and detector during the rotation, e.g., as in helical scanning methods. In this mode, the total z-translation during a complete rotation is typically comparable to or larger than the axial extent of the system. Thus, helical systems have been designed to perform relatively large translations to provide larger axial field of view. One exception is cardiac scanning, in which case the helical pitch is reduced so as to acquire temporal data of the cardiac motion.

VCT systems that use an array of source elements suffer from a sampling problem that derives from the fact that the source elements have discrete axial positions. In highly collimated systems, there may be gaps in the sampling. Axial planes corresponding to source element rows have both in-plane projection measurements (i.e., measurements where the source and detector are both in the same axial plane) and cross-plane projection measurements (i.e., measurements where the source and detector are in different axial planes), while axial planes between source element rows only have cross-plane projection measurements. Thus, intermediate planes between the source planes have different imaging characteristics than the source planes. In other words, due to the discrete z-positions of the source element rows, there is a z-dependence of the impulse response of the system. If the impulse response is z-dependent, the image quality of the reconstructed volume varies depending on the z-location. More specifically, the in-plane rays are necessary for sufficient sampling of the axial planes. Therefore, the axial planes corresponding to source element rows will be reconstructed more accurately than the planes between source element rows.

SUMMARY OF THE INVENTION

To solve this sampling problem, the invention provides a novel scanning method that comprises translations of the source relative to the subject in the z-direction (i.e., the axis of rotation) during the rotation. More specifically, as the source rotates through the angles of a single rotation, the source is simultaneously translated in the axial direction by a distance comparable to the source element spacing in the axial direction. Thus, in contrast to standard helical scanning methods, the total translation amount in a single rotation is generally comparable to the axial spacing between individual source elements, not to the total axial extent of the system.

The movement in the z-direction is designed so that the axial planes whose starting location is at discrete source element rows are not distinguished from axial planes starting at locations between the discrete source element rows, thereby reducing the z-dependence of the system and the associated sampling problem.

DETAILED DESCRIPTION

Figure 1:
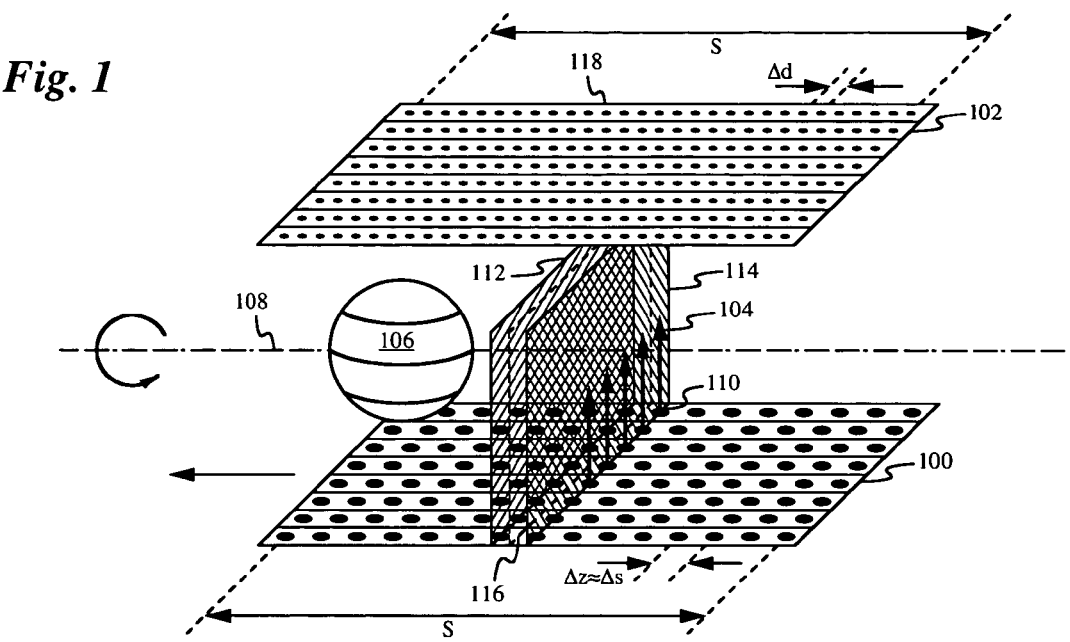
FIG. 1 illustrates a VCT system suitable for implementing the scanning method of an embodiment of the present invention wherein the source and detector arrays are both two-dimensional.

A preferred embodiment of the scanning method is implemented with a volumetric computed tomography system using a scanned anode x-ray source array 100 and an array of detectors 102, as shown in FIG. 1. During operation, x-rays 104 from the source 100 pass through an object 106 (such as the body of a patient) and are sensed by the detector 102 to produce an image. The source 100 and detector 102 are fixed to a gantry (not shown) that can rotate the source and detector together about a rotational axis 108 (also called the z-axis or axial direction). After a rotation by a small angle, another image is then acquired. The process is then repeated for a collection of N distinct rotational angles spanning a total rotational interval of $\Delta\theta$ and the images acquired at all the various angles are computationally combined to create a three-dimensional representation of the object. The total rotation $\Delta\theta$ is preferably 180 degrees or more. Although the x-rays shown in FIG. 1 appear to not diverge, in practice rays diverging in both the z and transverse directions are measured. The value of N depends on the size of the source and detector arrays and the divergence in the lateral direction. In a typical embodiment N is on the order of 100, i.e., images are collected at 100 distinct angles over a rotation of 360 degrees, so that $\Delta\theta/N$ is on the order of a few degrees.

The x-ray source 100 is preferably an array of discrete x-ray source elements, such as representative source element 110. In the context of this description, the term array is defined to include both a one-dimensional linear array and a two-dimensional planar or cylindrical array. Such an array has at least one column of discrete source elements 110 oriented parallel to the rotational axis 108 of the system (i.e., the z-axis) and multiple rows of discrete source elements 110 oriented perpendicular to the rotational axis 108 of the system. Note that in the case of a one-dimensional linear array, each row has just one source element 110. The source elements 110 are arranged in columns and rows of the array 100 with discrete spacing $\Delta s$ that is preferably uniform. The discrete spacing $\Delta s$ of a typical commercial source array 100 is likely to be approximately 3 mm or more. In the case of a cylindrical array, the source element rows form a circular arc rather than a line. The axial distance between the first and last rows of the source array is denoted S. Thus, the source array has $S/\Delta s+1$ source rows. Note that for purposes of illustration only, the array shown in FIG. 1 has a small number of source rows and columns. In one embodiment, the number of source rows and columns is 60 rows by 200 columns. The preferred distance between source elements is approximately 3 mm.

Axial planes of a VCT system are defined as x-y planes perpendicular to the z-axis. Source planes, such as adjacent source planes 112 and 114, correspond to axial planes containing source rows. Thus, source planes have a separation equal to the separation $\Delta s$ of source rows, i.e., typically 3 mm or more. Intermediate planes, such as plane 116 between source planes 112 and 114, are axial planes between source element rows.

Each source element 110 has an associated collimator (not shown) which limits the x-rays 104 produced by the source element so that they propagate towards the detector array, or a portion of the detector array. Specifically, the collimator limits the x-rays 104 of a source element 110 so that they are directed along lines of propagation from the source element 110 to at least one element in detector array 102, preferably to many such elements. Again, in the system illustrated in FIG. 1, the lines of propagation from each source are contained within a single source plane (i.e., in-plane rays), however the invention also applies to systems in which the lines of propagation are directed from the source element towards multiple detector rows (both in-plane and cross-plane rays).

The detector 102 acquires measurements of x-rays 104 that have propagated from the source 100, some of which may have also passed through the object 106. Preferably, the detector 102 is a one-dimensional or two-dimensional array of detector elements, such as representative detector element 118. The detector array 102 has one or more columns oriented parallel to the rotational axis 108 and multiple rows oriented perpendicular to the columns. In the case of a linear array, each row has just one element. The rows of a two-dimensional array may have the form of a circular arc or a line. Detector elements 118 preferably have a uniform spacing $\Delta d$ of approximately 1 mm or less, which is typically less than the spacing $\Delta s$ between source elements. Note that for purposes of illustration only, the detector array shown in FIG. 1 has a small number of rows and columns. In one embodiment, the detector has 144 rows and 48 columns. Detector and source components suitable for use in VCT systems described above are available from NexRay in Los Gatos, Calif.

Points on source planes, such as representative source planes 112 and 114, are sampled by both in-plane and cross-plane projection measurements, while points on intermediate planes, such as plane 116, only have cross-plane projection measurements. As a result, due to the discrete spacing $\Delta s$ of the source rows, there is a z-dependence of the impulse response of the system. In prior systems, this z-dependence of the impulse response produces corresponding z-dependent variations in the image quality of the reconstructed volume. More specifically, while the source planes have the benefit of in-plane rays, the intermediate planes do not. Consequently, the source planes will be reconstructed more accurately than the intermediate planes.

To solve this sampling problem, embodiments of the present invention provide a scanning method that includes translations of the source relative to the subject in the z-direction (i.e., the axis of rotation) during the gantry rotation. More specifically, as the source and detector rotate through the angles of a single rotation they are simultaneously translated in the z-direction by a distance $\Delta z$ that is on the same order as the source element spacing $\Delta s$ in the axial direction. In other words, values of $\Delta z$ may be equal to a substantial fraction of $\Delta s$ (e.g., ¼ or *more*), or equal to a small multiple of $\Delta s$ (*e.g.*, 4 or less). Thus, in contrast to helical scanning methods, the total translation amount $\Delta z$ in a single rotation is generally comparable to the spacing $\Delta s$ between individual source elements, not to the total axial extent of the system S. As an example, the total translation during a single rotation could be equal to the spacing $\Delta s$ between sources in the z-direction (i.e., about 3 mm or more). Although this is the preferred translation, other translations could also be used, such as integer multiples $n\Delta s$ of the source spacing, for a small positive integer n. Consider as an example the case where n=1. As the gantry is rotated to each of the N distinct rotational angles during one rotation through a total angle $\Delta\theta$, the gantry is also translated to N distinct translation positions to produce a total translation $\Delta z$. Thus, between each distinct sampling angle and position, the gantry is rotated by an angle of $\Delta\theta/N$ and translated by a distance of $\Delta z/N$. This produces, for k=1, 2, . . . ,N, a sequence of rotational angles $k\Delta\theta/N$ and corresponding translation distances $k\Delta z/N$. It will be appreciated that the translation and the rotation may be discrete steps or continuous motions.

The small translation movements in the z-direction over the course of the entire rotation is designed so that the axial planes passing through discrete source row positions are not distinguished from axial planes passing between the discrete source row positions, thereby eliminating the z-dependence of the system and the associated sampling problem. Thus, it is preferably that the N translation positions are uniformly spaced within the total distance $\Delta z$.

To reconstruct a volume acquired by a system with multiple source elements, conventional computer algorithms rebin the acquired data into a standard geometry, for example parallel ray projections. For use with the scanning technique of the invention, the algorithm would be provided with the precise translation of the source and detector, and would use this translation during the rebinning to calculate the geometry of each ray.

Figure 2:
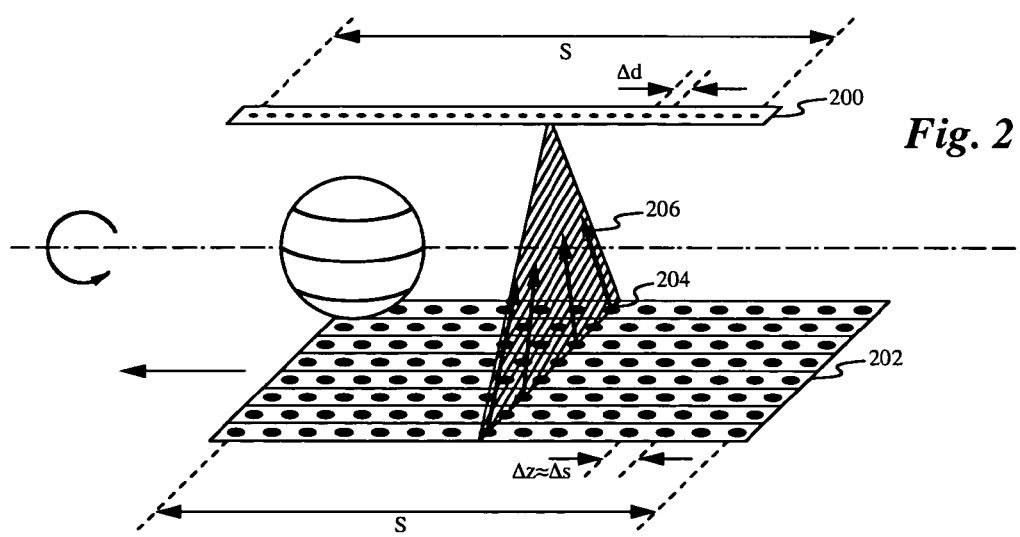
FIG. 2 illustrates a VCT system suitable for implementing the scanning method of an embodiment of the present invention wherein the source array is two-dimensional and the detector array is one-dimensional.
Figure 3:
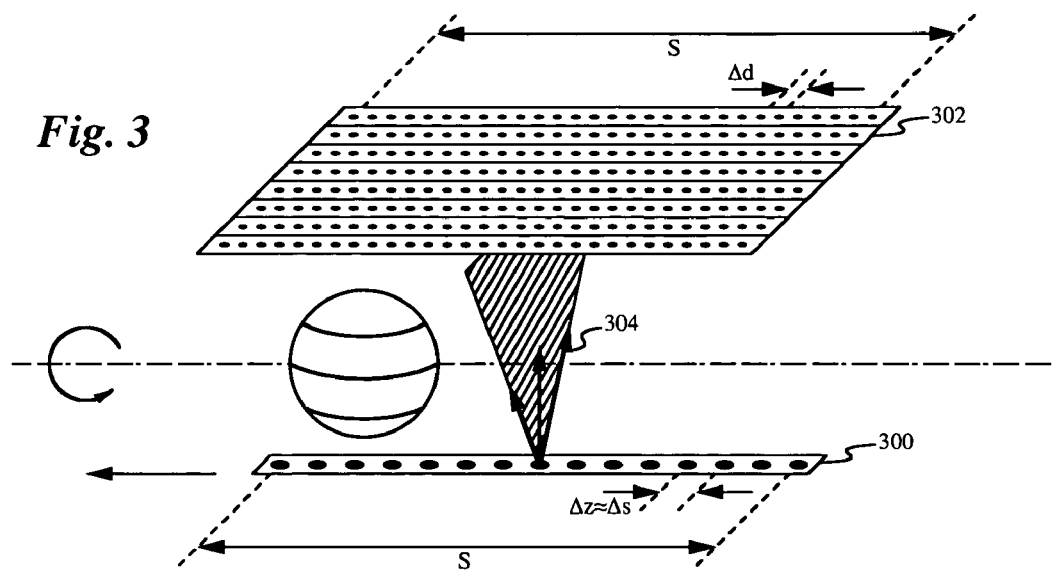
FIG. 3 illustrates a VCT system suitable for implementing the scanning method of an embodiment of the present invention wherein the source array is one-dimensional and the detector array is two-dimensional.

The scanning techniques of the present invention apply generally to any VCT system whose source has multiple elements positioned at discrete locations in the z-direction. There are many possible designs for such a system. For example, FIG. 2 shows a VCT system with a linear detector array 200 (i.e., having just one column of detector elements) and a planar source array 202. The source elements, such as representative element 204, have collimators that direct the x-rays toward the linear detector array 200. In the particular system illustrated in FIG. 2, x-rays 206 from source elements in a common row are all directed within the same source plane to converge at a single detector element. The invention also applies to systems where the x-rays from a source element are directed towards multiple detector rows. The system of FIG. 2 is otherwise identical to the system described above in relation to FIG. 1. Another example of a VCT system with discrete source rows is shown in FIG. 3. In this system the source array 300 is a linear array, while the detector array 302 is a planar array. Each of the source elements 304 has a collimator that limits the x-rays 304 from the source towards the detector array. In the illustrated system, the x-rays are collimated to a fan-shaped beam within a source plane, however the invention also applies to systems where the x-rays are collimated to a cone-shaped beam. The system of FIG. 3 is otherwise identical to the system described above in relation to FIG. 1.

Figure 4:
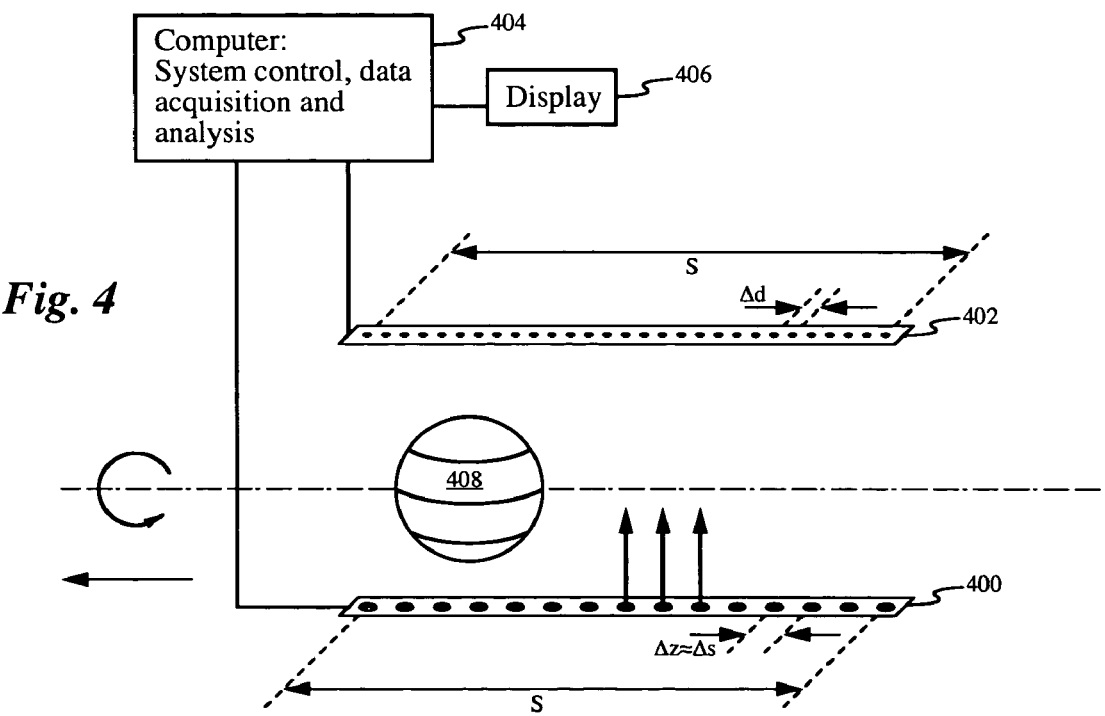
FIG. 4 illustrates a VCT system suitable for implementing the scanning method of an embodiment of the present invention wherein the source and detector arrays are both one-dimensional.

A VCT system whose source array 400 and detector array 402 are both linear arrays is shown in FIG. 4. The system of FIG. 4 cannot detect rays that diverge in the lateral direction, but it can have divergence in the z direction. To collect data for 3D reconstruction, since this system has only a single source column and a single detector column, it uses translation of the source and detector in the lateral direction as well as rotation about the axis of rotation. It is also possible to build VCT systems that use no rotation at all. An example are the so-called electron beam CT scanners that are known in the art. The target rings in these scanners are x-ray sources that are displaced from each other in the z direction. It is also conceivable to build VCT scanners in which sources and detectors wrap around the object, either on the same or different cylinders. The present invention can be used in these systems that require no mechanical rotation, but which have sources displaced from each other in the axial direction.

Also shown in FIG. 4 is a computer 404 which controls the operation of the system, acquires data, analyzes the data to produce a reconstructed three-dimensional representation of object 408. Various renderings of the three-dimensional representation may be (optionally) displayed on a display device 406. The computer 404 controls the timing of the emission of x-rays from the source array 400, controls the angle and z-translation movements of the source 400 and detector 402, manages the acquisition and storage of image data from the detector 402, processes the image data to produce a reconstructed three-dimensional representation of object 408, and produces rendered image slices or other views derived from the reconstructed three-dimensional representation suitable for display. Each of the VCT systems of FIGS. 1–3 has an identical computer system except for the differences that pertain to the different source and detector designs.

The invention claimed is:

1. A method for volumetric computed tomography comprising: emitting x-rays from a source;
measuring the transmission of x-rays through an object with a detector array;
translating the source and detector through a translation distance $\Delta z$ in an axial direction concurrently with the measurement of x-ray transmission;
reconstructing a three-dimensional representation of a portion of the object from the measured x-ray transmission;
wherein the source comprises a plurality of discrete x-ray source elements spanning a distance S in the axial direction, wherein two adjacent source elements have location displaced from each other by a source spacing distance $\Delta s$ in the axial direction; wherein x-rays from each of the discrete x-ray source elements are directed to multiple detector rows; wherein rows of the detector array measure both in-plane and cross-plane x-rays; and
wherein the translation distance $\Delta z$ is significantly less than S and at most four times the source spacing distance $\Delta s$.

2. The method of claim 1 wherein the translation distance $\Delta z$ is equal to an integer multiple of the spacing distance $\Delta s$.

3. The method of claim 1 wherein the translation in the axial direction during the measurement is performed at a substantially constant speed.

4. The method of claim 1 further comprising rotating the source and detector about the object by an angle $\Delta \theta$ during the measuring and translating.

5. The method of claim 4 wherein translating the source and detector comprises translating the source and detector to a number N of translation positions separated from each other by a uniform distance $\Delta z/N$.

6. A volumetric computed tomography system comprising:
an x-ray source array comprising a plurality of discrete x-ray source elements arranged in source rows displaced from each other by a source spacing distance $\Delta s$ in an axial direction of the system and spanning a distance S in the axial direction;
an x-ray detector array;
translation means for translating the source and detector together through a translation distance $\Delta z$ in said axial direction, wherein the translation distance $\Delta z$ is less than S and at most four times the source spacing distance $\Delta s$; and
data acquisition means for acquiring x-ray transmission measurements using said source and detector at a number of translation positions in said axial direction;
wherein x-rays from each of the discrete x-ray source elements are directed to multiple detector rows; and
wherein rows of the detector array acquire x-ray transmission measurements from both in-plane and cross-plane x-rays.

7. The system of claim 6 wherein said system also comprises image reconstruction means to reconstruct a three-dimensional representation of a portion of an object from said x-ray transmission measurements.

8. The system of claim 6 wherein the translating in the axial direction is at a substantially constant speed.

9. The system of claim 6 wherein the source and detector rotate about the axial direction of the system by an angle $\Delta \theta$ during the acquiring of x-ray transmission measurements.

10. The system of claim 6 wherein the source and detector rotate and translate together to a plurality of uniformly spaced rotation angles within a rotation angle $\Delta \theta$ and a corresponding plurality of translation positions within the translation distance $\Delta z$.

11. The system of claim 6 wherein the translation distance $\Delta z$ is equal to an integer multiple of the spacing distance $\Delta s$.

12. The system of claim 6 wherein the translation distance $\Delta z$ is equal to the spacing distance $\Delta s$.

13. The system of claim 6 wherein the translation distance $\Delta z$ is at most 3 mm.

* * * * *